US005795752A

United States Patent [19]
Smith

[11] Patent Number: 5,795,752
[45] Date of Patent: Aug. 18, 1998

[54] METHOD FOR CREATING SUPERINDUCED CDNA LIBRARY & ISOLATING LIGAND-STIMULATED GENES

[75] Inventor: Kendall A. Smith, Hanover, N.H.

[73] Assignee: Trustees of Dartmouth College, Hanover, N.H.

[21] Appl. No.: 330,108

[22] Filed: Oct. 27, 1994

Related U.S. Application Data

[63] Continuation of Ser. No. 104,736, Aug. 10, 1993, abandoned, which is a continuation of Ser. No. 796,066, Nov. 20, 1991, abandoned.

[51] Int. Cl.$^6$ .............................. C12N 15/00; C12N 1/20
[52] U.S. Cl. ................................ 435/172.3; 435/252.3; 435/320.1
[58] Field of Search ........................... 435/172.3, 252.3, 435/320.1

[56] References Cited

FOREIGN PATENT DOCUMENTS 8810304    6/1988    WIPO

OTHER PUBLICATIONS

"Analysis of cDNA Inserts" and Generation of a Complete cDNA Library in Sambrook et al. *Molecular Cloning: A Laboratory Manual* (New York: Cold Spring Harbor Laboratory, 1989)2: 8.76–8.77.

Abdollahi, A. et al. (1991) "Sequence and expression of a cDNA encoding MyD118: a novel myeloid differentiation primary response gene induced by multiple cytokines" *Oncogene* 6: 165–167.

Bowie, Y. et al. (1994) "Cloning and Expression of a cDNA for the Human Prostanoid IP Receptor" *J. Biol. Chem.* 269(16): 12173–12178.

Dickinson, L.A. et al. (1992) "A Tissue–Specific MAR/SAR DNA–Binding Protein with Unusual Binding Site Recognition" *Cell* 70:631–645.

Feder, J. et al. (1993) "A Rat Gene with Sequence Homology to the Drosophila Gene hairy Is Rapidly Induced by Growth Factors Known To Influence Neuronal Differentiation" *Mol. Cell. Biol.* 13(1): 105–113.

Hong, J.X. et al. (1993) "Isolation and Characterization of a Novel B Cell Activation Gene" *J. Immunol.* 150(9): 3895–3904.

Papathanasiou, M.A. et al. (1991) "Induction by Ionizing Radiation of the gadd45 Gene in Cultured Human Cells: Lack of Mediation by Protein Kinase C" *Mol. Cell. Biol.* 11(2): 1009–1016.

Selten, G. et al. (1986) "The Primary Structure of the Putative Oncogene pim–1 Shows Extensive Homology with Protein Kinases"0 *Cell*, 46: 603–611.

Siderovski, D.P. et al. (1994) "A Human Gene Encoding a Putative Basic Helix–Loop–Helix Phosphoprotein Whose mRNA Increases Rapidly in Cycloheximide–Treated Blood Mononuclear Cells" *DNA and Cell Biology* 13(2): 125–147.

Smith, M.L. et al. (1994) "Interaction of the p53–Regulated Protein Gadd45 with Proliferating Cell Nuclear Antigen" *Science* 266:1376–1380.

Waksman, G. et al. (1993) "Binding of a High Affinity Phosphotyrosyl Peptide to the Src SH2 Domain: Crystal Structures of the Complexed and Peptide–free Forms" *Cell* 72:779–790.

Melvin, W.T. and Keir, H.M. (1977) *Biochem. J.* 168:595. Science 227:1240–1243, 8, Mar. 1985, Cramer, Rapid Switching of Plant Gene Expression Induced by Fungal Elicitor.

Biochem & Biophys. Res. Comm., 129: 618–625, 28, Jun. 1985, Forsdyke, cDNA Cloning of mRNA, Which Increases Rapidly in Human Lymphocytes Cultured With Coneavalsi – . . . .

Van Obberghen–Schilling et al. (1982) Biochemical and Biophysical Research Communications, vol. 106: 79–86.

Cochran et al. (1984) Cell, vol. 33:939–947.

Stetler et al. (1984) Proc. Natl. Acad. Sci. USA, vol. 81:1144–1148.

Hatakeyama et al. (1985) Nature, vol. 318:467–470.

Kondo et al. (1986) Nature, vol. 320:75–77.

Kuo et al. (1986) The Journal of Immunology, vol. 137:1538–1543.

Reed et al. (1986) Proc. Natl. Acad. Sci. USA, vol. 83:3982–3986.

Sabath et al. (1986) Proc. Natl. Acad. Sci. USA, vol. 83:4739–4743.

Sharon et al. (1986) Science, vol. 234:859–863.

Stern et al. (1986) Science, vol. 233:203–206.

Zakut–Houri et al. (1987) Gene, vol. 54:105–111.

Alemendral et al. (1988) Molecular and Cellular Biology, vol. 8:2140–2148.

Dautry et al. (1988) The Journal of Biological Chemistry, vol. 263:17615–17620.

Johnson et al. (1988) Proc. Natl. Acad. Sci. USA, vol. 85:6072–6076.

Telerman et al. (1988) Molecular and Cellular Biology, vol. 8:1498–1503.

Woodford et al. (1988) Analytical Biochemistry, vol. 171:166–172.

Johnson et al. (1990) The Journal of Immunology, vol. 145:1144–1151.

Sabath et el. (1990) The Journal of Biological Chemistry, vol. 265:12671–12678.

Zmuidzinas et al. (1991) Molecular and Cellular Biology, vol. 11:2794–2803.

*Primary Examiner*—John Ulm
*Attorney, Agent, or Firm*—Pretty, Schroeder & Poplawski; Vivana Amzel

[57] ABSTRACT

Disclosed is a method of producing a complementary DNA (cDNA) library enriched in ligand-inducible genes of a cell. The method includes activating a cellular ligand receptor for a predetermined period of time in the presence of labelled RNA precursors and a substance which enhances the level of RNA in said cell. The RNA presursors are incorporated into the RNA synthesized by said cell in response to receptor activation. The labelled RNA is separated from unlabelled RNA and used to prepare cDNA. The cDNA is cloned into host cells to provide a cDNA library of cDNA-containing clones. This library can then be screened for clones containing ligand-inducible genes.

33 Claims, 5 Drawing Sheets

METHOD FOR CREATING SUPERINDUCED CDNA LIBRARY & ISOLATING LIGAND-STIMULATED GENES

This application is a continuation of application Ser. No. 08/104,736, filed 10 Aug. of 1993, now abandoned, which is a continuation of application Ser. No. 07/796,066, filed 20 Nov. of 1991, now abandoned.

The work leading to this invention was partially supported under National Institute of Health Grant No. R01CA-1 7643. The United States Goverment may have rights in this patent.

BACKGROUND OF THE INVENTION

Mammalian cell growth, differentiation, and migration are directed by hormones and specific protein ligands, often termed cytokines. In particular, cells comprising the neuroendocrine, hematopoietic and the immune/inflammatory systems are known to be governed by cytokines. Cytokines, like other ligands, interact with cells by means of specific receptors, usually expressed on the cell surface.

A fundamental problem confronting biomedical scientists is to discern how signals are transduced through ligand receptors and how these signals determine the response of the cell. Many ligands influence their target cells by stimulating the expression of specific genes. However, the genes signaled by most cytokines remain largely unknown owing to the complexity of cellular biochemistry. Moreover, the gene products that are vital for performing different cellular processes are often only expressed transiently, and/or in very low concentrations so that they are difficult to detect, isolate and characterize.

Interleukin-2 (IL-2) is a cytokine that is critical for the immune system: it directs the proliferation and differentiation of T lymphocytes (T-cells), B lymphocytes (B-cells), and natural killer (NK) cells. Just how IL-2 signals these cellular events in the various types of target cells remains unknown. A few genes have been identified that are expressed as the result of IL-2 stimulation of T cells. These include the cellular proto-oncogenes c-fos, c-mob, c-myc, pim-1, and c-raf-1. However, exactly how many and what other genes are expressed as a result of IL-2/IL-2 receptor interaction remains unknown.

Since the discovery of DNA cloning, methods have become available to isolate specific genes expressed by cells. However, it has been difficult to devise new methods to isolate and clone all or most of the genes expressed by a cell activated by a given ligand, a task that must be done before one can understand how the ligand directs the cell to perform specific functions. In addition, methods of identifying a particular gene or genes stimulated early on after ligand receptor activation have not been easily forthcoming as the number of genes stimulated by receptor activation from which a particular gene must be selected is usually quite large.

Therefore, what is needed are methods to select and enrich only for those genes stimulated by a given ligand. Ideally, these methods should detect those genes expressed in low concentrations, as well as those expressed at high concentrations.

SUMMARY OF THE INVENTION

This invention pertains to complementary deoxyribonucleic acid (cDNA) libraries enriched in clones containing genes induced by ligand stimulation of a cell having a corresponding receptor for the ligand, and to methods of producing the same. This invention also relates to the genes which are expressed immediately or early on as a consequence of such a ligand-receptor interaction, and to methods of identifying these genes.

In the method of producing a cDNA library enriched in ligand-inducible genes, a cellular ligand receptor on a cell is activated with a ligand, for a predetermined period of time, to induce expression of those genes expressed as a result of ligand-receptor binding. Useful ligands include any of those which can activate a specific cellular receptor. These include natural or synthetic ligands for the receptor. Ligands include cytokines such as the interleukins, cellular growth factors, colony stimulating factors, hormones, peptides, antibodies, and receptor-binding fragments thereof.

The cells are activated with the ligand in the presence of labelled RNA precursors. These precursors are incorporated into RNA synthesized by the cell in response to receptor activation. Labelled precursors are used in order to distinguish newly transcribed RNA from unlabelled, preexisting RNA. Preferred labelled RNA precursors include 6-thioguanine, 4-thiouridine, and tritiated uridine.

Activation is also carried out in the presence of a substance which enhances the level of RNA in a cell. Preferred substances include the protein synthesis inhibitors, cycloheximide and puromycin. Other useful substances include cyclic 3', 5'-adenosine monophosphate (cAMP), analogs of cAMP such as dibutyryl cAMP, and other molecules which increase the intracellular level of cAMP. The labelled RNA is then separated from the unlabelled RNA and used to prepare cDNA.

The cDNA is cloned into host cells to provide a cDNA library of cDNA-containing clones. This library is then screened for clones containing ligand-inducible genes.

In one embodiment of the invention, the screening step includes probing the cDNA library with a DNA probe constructed from total cellular RNA or mRNA derived from (1) a ligand-induced cell and from (2) an uninduced cell. The library is probed under conditions such that the probe hybridizes specifically with complementary cDNA sequence in the first library. The selecting step includes selecting those clones containing sequences that hybridize only with probes constructed from ligand-induced mRNA or total RNA.

By following the method of the invention, a cDNA library of clones enriched in genes induced by ligand binding have been prepared. Some of these clones contain the DNA sequences set forth in the Sequence Listing as SEQ ID NOS: 1–19.

BRIEF DESCRIPTION OF THE FIGURES

The foregoing and other objects of this invention, the various features thereof, as well as the invention itself, may be more fully understood from the following description, when read together with the accompanying drawings, in which:

FIG. 1A, clone 1A8: FIG. 1B, clone 10A8; FIG. 1C, clone 10F9; FIG. 1D, clone 1F5; FIG. 1E, clone 10D6; FIG. 1F, clone 11B2; FIG. 1G, clone 10E6; FIG. 1H, clone 13E2;

FIG. 2A, clone 1A8, FIG. 2B, clone 10D6; FIG. 2C, clone 13E2; FIG. 2D, clone 1F5; FIG. 2E, clone 10A8; FIG. 2F, clone 10F9; FIG. 2G, clone 11B2; FIG. 2H, clone 11E6;

FIG. 3A, clone 10A6; FIG. 3B, clone 1A8; FIG. 3C, clone 1F5; FIG. 3D, clone 10A8; FIG. 3E, clone 10F9; FIG. 3F, clone 11B2; FIG. 3G, clone 11E6; FIG. 3H, clone 13E2;

FIG. 5A, clone 1A8, FIG. 5B, clone 10D6; FIG. 5C, clone 1F5; FIG. 5D, clone 10A8; FIG. 5E, clone 10F9; FIG. 5F, clone 11B2; FIG. 5G, clone 11E6; FIG. 5H, clone 13E2.

DESCRIPTION OF THE INVENTION

Figure 1:
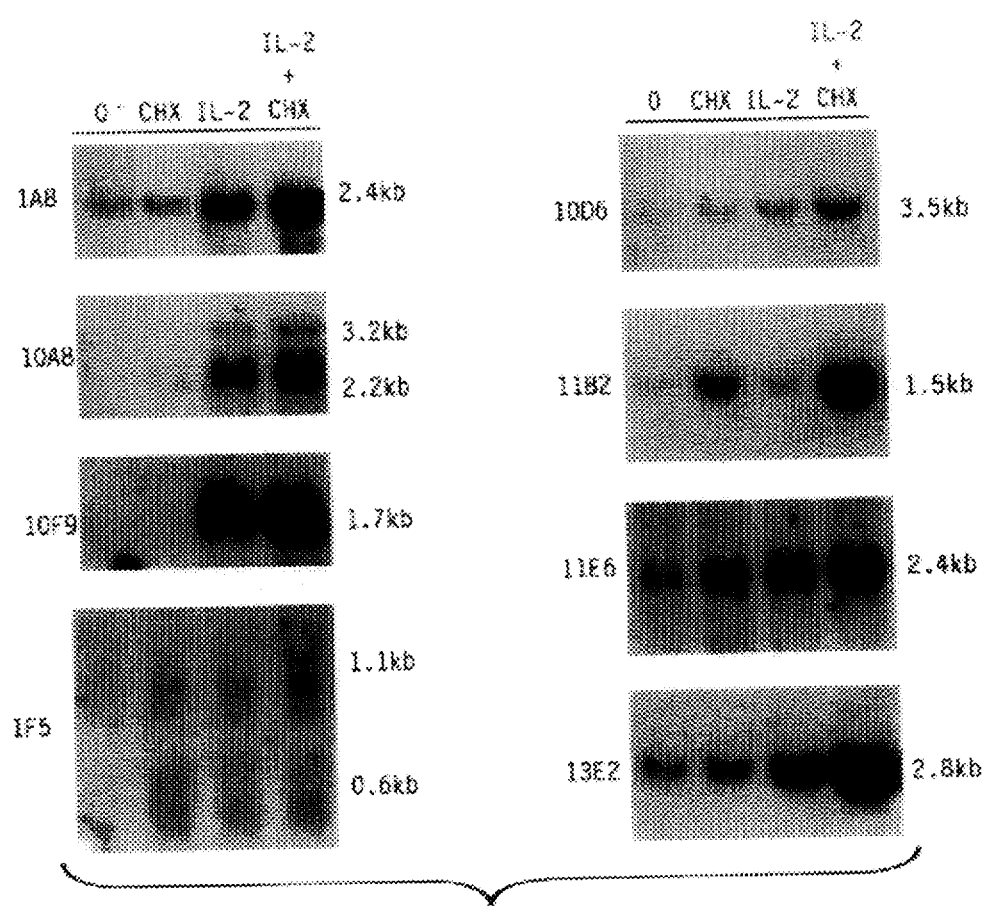
FIGS. 1A–1H are photographic representations of Northern blots using RNA isolated from uninduced and induced (with CHX, IL-2, or IL-2+CHX) T-cells and the following cloned cDNA probes.
Figure 2:
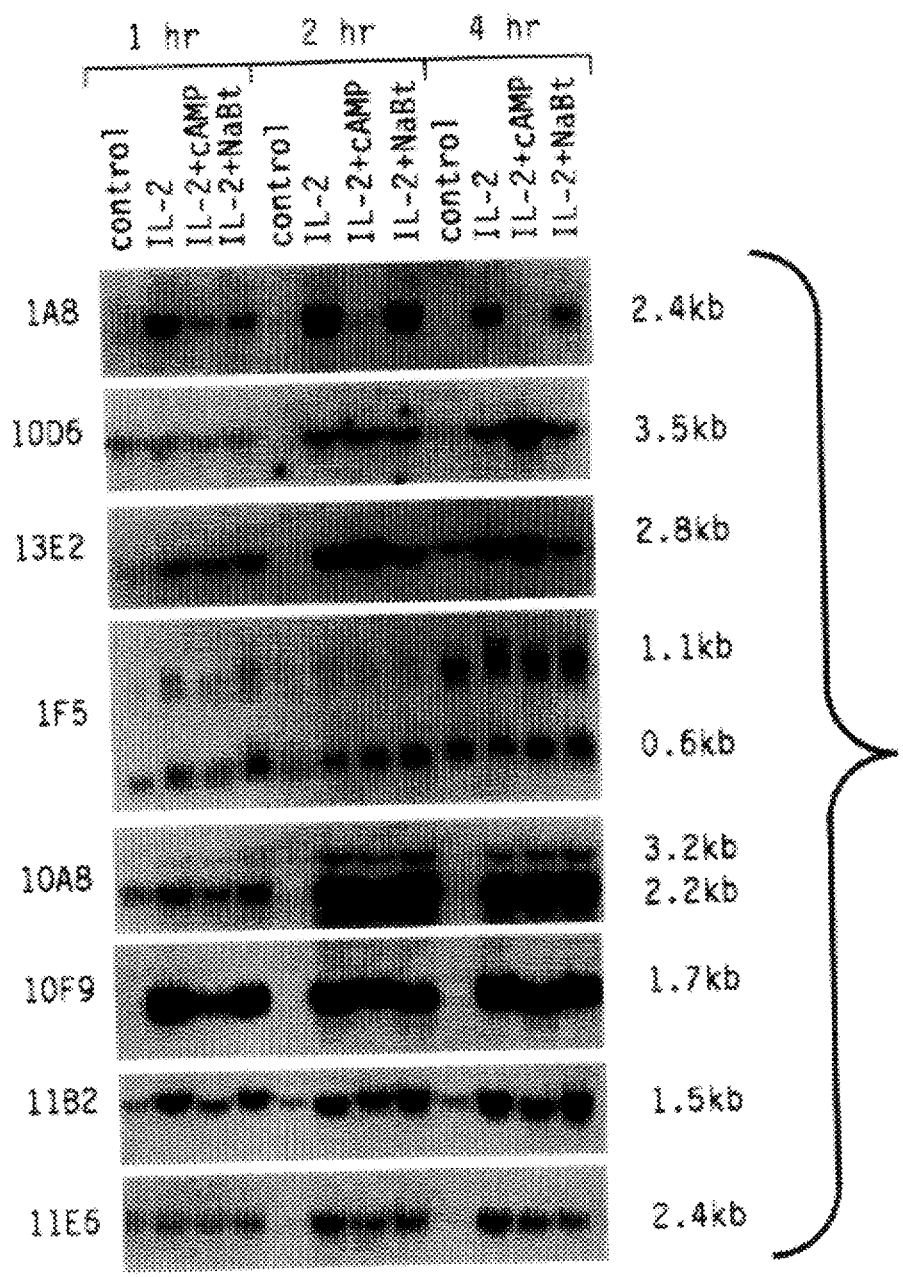
FIGS. 2A–2H are photographic representations of Northern blots using RNA isolated from control and IL-2-induced (in the presence or absence of cAMP or NaBt) T-cells and the following cloned cDNA probes.
Figure 3:
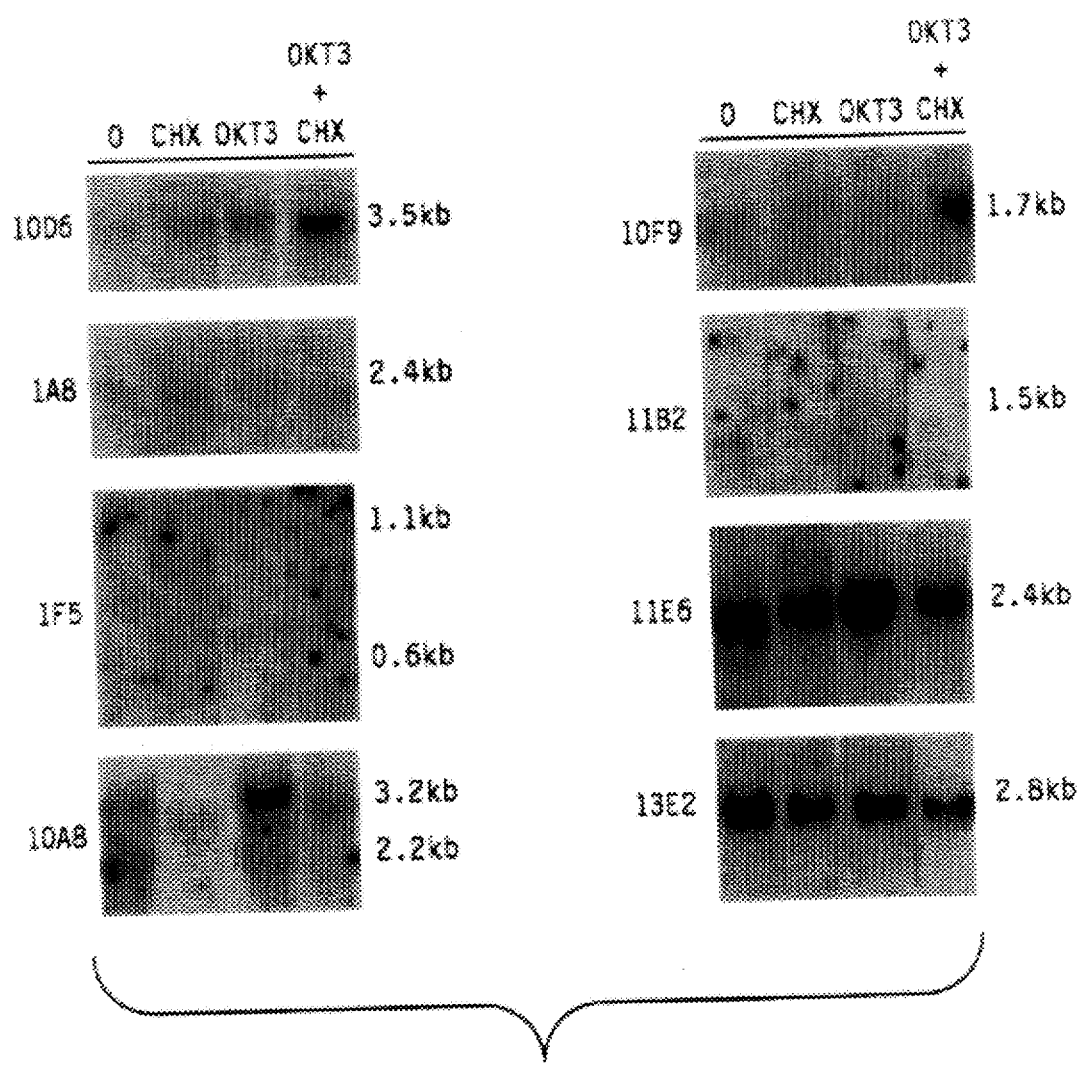
FIGS. 3A–3H are photographic representations of Northern blots using RNA isolated from T-cells whose T-cell antigen receptor had been untreated or treated (with CHX, antibody OKT3, or OKT3+CHX) and the following cloned cDNA probes.

By combining several different procedures, a cDNA library can be constructed which is enriched in clones containing genes whose expression is induced by activation of a cellular ligand-specific receptor. This enriched library can facilitate identification and characterization of ligand-activated genes that are triggered immediately and/or early on after receptor activation (e., 2 to 4 hours after the ligand binds to its receptor). Such genes may play a role in stimulating growth phase transitions and subsequent clonal expansion of a particular cell type.

The method of the invention can be used to create cDNA libraries of the genes induced by activation of a variety of different cellular receptors. The receptors can be cytoplasmic, nuclear, or cell-surface receptors, and include receptors for cytokines, hormones, factors, and peptides. For example, cytokines such as the interleukins (e.g., IL-1 and IL-2), cellular growth factors (e.g., platelet-derived growth factor (PDGF), epidermal growth factor (EGF), fibroblast growth factor (FGF), insulin-like growth factor (IGF)), colony stimulating factors (e.g., multiplication stimulating activity), and hormones (e.g., insulin, somatomedin C, and steroid hormones) are useful as activators of certain cellular receptors.

The ligand used to activate the receptor can be the natural ligand recognized by the receptor or a synthetic analog. Alternatively, an anti body specific for the receptor and capable of activating the receptor may be used.

The receptor is activated by a ligand or other activation for a predetermined length of time and at a concentration necessary to activate the receptor. This activation is carried out in the presence of labelled RNA precursors which are incorporated into the RNA synthesized by the cell in response to receptor activation. Thus, the RNA transcribed is labelled so as to be distinguished from preexisting RNA which is not labelled.

Some labels (such as radiolabels) may be employed to monitor the newly synthesized RNA. Useful radiolabelled RNA precursors for such purposes include [$^3$H]-uridine. Other labels may be used to separate newly transcribed RNA from unlabelled RNA. For example, RNA synthesized from thiol-labelled RNA precursors specifically adheres to phenylmercury agarose (Woodford et al. (1988) *Anal. Biochem.*

1781:166–172). RNA newly synthesized in response to receptor activation can be separated from preexisting RNA in the cell; all RNA molecules expressed prior to ligand-activation pass through the phenylmethyl mercury column, Leaving only the newly synthesized, thiol- (SH-) labelled RNA attached to the agarose via a covalent bond between the mercury and sulfur. The thiol-labelled RNA molecules are then eluted from the column by reducing the Hg—S bond with an excess of 2-mercaptoethanol.

To augment the expression of immediate/early ligand-activated genes which may be difficult to identify because of the large number of downstream genes turned on at a later time, a substance that enhances the level of RNA is added to the culture medium during the ligand stimulation (see, e.g., Cochran et al. (1983) *Cell* 33:939–947). Useful substances include those compounds that stabilize RNA and/or that block translation, thereby blocking feedback inhibition of these genes by a later gene product. Such activity may potentiate the magnitude of the RNA expressed as well as the duration of the life of the RNA. Examples of such useful substances include cyclohexamide (CHX), which inhibits protein synthesis at the level of RNA-ribosome complexing and may stabilize polysomal RNA, and puromycin, which inhibits translation by causing premature dissociation of the peptide-mRNA-ribosome complex.

cAMP is another useful substance which enhances the level of RNA. Increased levels of cAMP, or analogs or agents that elevate cAMP levels, such as forskolin, dibutyryl AMP, and isobutylmethyl xanthene, are known to inhibit cell growth, proliferation, and inositol phospholipid turnover. In addition, elevated levels of cAMP completely inhibit IL-2-stimulated T-cell proliferation (Johnson et al. (1988) *Proc. Natl. Acad. Sci.* (USA) 85:6072–6076).

The labelled RNA transcribed consequent to receptor activation in the presence of the substance which enhances RNA levels is then purified from the cytoplasm of the cells. Purification can be accomplished by extracting total cellular RNA from a cell homogenate or fraction thereof, isolating mRNA therefrom, for example, using a poly U or poly[dT] column, and then separating the labelled RNA from the unlabelled RNA. Separation can be accomplished, for example, using the phenylmethyl mercury agarose protocol described above. Of course, other known methods of separating the newly synthesized RNA from the preexisting may be used as well.

The cDNA libraries can be prepared from the separated labelled RNA by standard techniques. For example, the labelled RNA may be reversed transcribed into cDNA, using oligo[dT] primers. The cDNA is then ligated into appropriate vectors using established recombinant DNA techniques. A cDNA library is then constructed by methods well known in the art in prokaryotic or eucaryotic host cells that are capable of being transfected by the vectors.

Prokaryotic systems most commonly utilize *E. coli* as host, although other bacterial strains such as Bacillus, Pseudomonas, or other Gram-positive or Gram-negative prokaryotes can also be used. When such prokaryotic hosts are employed, operable control systems compatible with these hosts are ligated to the cDNA fragments and disposed on a suitable transfer vector which is capable of replication in the bacterial host cell. Backbone vectors capable of replication include phage vectors and plasmid vectors, as is known in the art. Common plasmid vectors include those derived from pBR322 and the pUC series. One such useful vector which is commercially available is the plasmid pBluescriptTIISK+ (Stratagene, La Jolla, Calif.). Charon lambda phage is a frequently employed phage vector. Control sequences obligatorily include promoter and ribosome binding site encoding sequences, and a variety of such controls are available in the art, such as the beta-lactamase (pencillinase) and lactose (lac) promoter systems (see, e.g., Chang et al. (1977) *Nature* 198:106), and the tryptophan (trp) promoter systems (Goeddel et al. (1980) *Nucleic Acids Res.* 8:4057. Composite promoters containing elements of both the trp and lac promoter systems are also available in the art.

Eucaryotic microbes, such as laboratory strains of *Saccharomyces cerevisiae*, or Baker's yeast, may also be used for expression. A number of yeast control systems and vectors are available, including those which are promoters for the synthesis of glycolytic enzymes (see, e.g., Hess et al. (1968) *Biochem.* 17:4900). Yeast vectors employing the 2 micron origin of replication are suitable as transfer vectors (see, e.g., Broach (1982) *Meth. Enzym.* 101:307).

Tissue cultures of insect cell lines, or cell lines immortalized from mammalian or other higher organisms have also been used as recombinant hosts. Such cell lines include chinese hamster ovary (CHO), Vero, HeLa, and COS cells. In general, the COS cell system is used for transient expression, while CHO cells typically integrate transformed DNA into the chromosome. Suitable mammalian vectors are generally based on viral origins of replication and control sequences. Most commonly used are the simian virus 40 (SV40) promoters and replicons (see Fiers et al. (1978) *Nature* 273:113) and similar systems derived from Adenovirus 2, bovine papilloma virus, and avian sarcoma virus.

The ligand-activated genes are then screened in the library using any one of several different methods. One method involves differential hybridization with cDNA probes constructed from mRNA derived from ligand-activated cells and unactivated cells. Another method includes hybridization subtraction, whereby cDNA from ligand-activated cells is hybridized with an excess of mRNA from unactivated cells to remove RNA molecules common to both. Alternatively, cDNA probes can be made from the same pool of thiol-selected mRNA used to make the cDNA library, as these sequences are highly enriched for ligand-induced molecules. One can prepare cDNA probes from mRNA extracted from cells treated with drugs that block the biologic response to the particular cytokine (e.g., rapamycin blocks the proliferative response of T cells to IL-2, and cyclosporine and FK506 block the T-cell response to activation via the T-cell antigen receptor). Results from probing with the cDNA made from drug-inhibited cells can then be compared to results from probes made from cells not inhibited by these drugs.

The marked superinduction observed for a number of the genes using a substance, such as CHX, which enhances RNA levels is crucial in enabling their detection by differential hybridization, as it has been estimated that differential hybridization is only effective in the detection of relatively high-abundance RNAs expressed at a level of greater than 500 copies per cell. Therefore, the superinduction increases that level of expression of low-abundance RNAs above the threshold of detection by differential screening. In addition, the approximately 10-fold enrichment for newly synthesized RNA afforded by the thiol-labelling procedure further heightens the efficacy of the cloning procedure. Thus, the combination of superinduction and thiol-labelling of RNA significantly enhances the sensitivity of differential screening, and provides a cloning strategy which has the capacity to detect messages normally present in relatively low abundance (i.e., less than 100 copies/cell.

After the initial screening of the cDNA library, all clones isolated as tentatively positive must be corroborated as truly ligand-activated. This can be accomplished by isolating the cDNA insert from each cloned plasmid, and then employing this cDNA to probe RNA from ligand-activated cells by Northern blot analysis.

Then, to identify each gene, the cDNA may be subjected to sequence analysis. Searches of the GenBank (Los Alamos, N.Mex.) and EMBL (Heidelberg, Germany) data bases may be made of even partial sequences to identify known sequences such as pim-1. (SEQ ID NO:20), a previously characterized, IL-2 induced gene.

A number of methods can be used to characterize the novel ligand-enhanced genes and begin to determine their functional roles in, for example, signal transduction. DNA sequence analysis of the cDNA of the mRNA transcript can predict the coding region for the gene product and the amino acid sequence. From the amino acid sequence, the gene product can be placed into one of several categories of proteins, such as DNA-binding proteins, kinases, phosphatases, transmembrane proteins, or secreted products. These categories then will predict certain obvious functions and characteristics to be examined.

For example, the mechanism whereby IL-2 binding to its heterodimeric p55/p75 receptor on the cell surface activates specific gene expression is not well understood. The 75 kD component of the IL-2 receptor, which is responsible for signal transduction, does not exhibit sequence homologies indicative of previously characterized functional domains. However, the involvement of protein phosphorylation in the IL-2 response has been indicated by the activation of IL-2R-associated kinases, including the tyrosine kinase $p56^{lck}$, as well as the cytoplasmic serine/threonine kinase c-raf-1 in early IL-2-mediated transmembrane signalling. In addition, a number of proteins, including the IL-2R p75, are rapidly phosphorylated in response to IL-2. The hydrolysis of phosphatidylinositol glycan is also stimulated by IL-2, resulting in the formation of the putative second messengers myristylated diacylglycerol and inositol phosphate-glycan. Analysis of the regulatory elements governing expression of the immediate-early genes described in the present study will be useful in the further characterization of the secondary biochemical messengers activated by the IL-2 receptor.

Other methods helpful in determining the functional relevance of the IL-2-induced genes include examining T-cells for their expression in response to triggering of other receptors.

One such receptor is the T-cell antigen receptor. Seminal studies of the T-cell system have demonstrated that T-cell activation occurs as a two-step process. Quiescent cells are initially stimulated through engagement of the antigen receptor, which provides the cells with the capacity to produce and respond to IL-2. Subsequently, the interaction of IL-2 with its cell-surface receptor drives progression through the $G_1$ to the S phase of the cell cycle. Transmembrane signalling through both the T-cell antigen receptor has been shown to trigger the heightened expression of a number of genes, including c-fos, c-myc and c-raf-1 (Reed et al. (1986) *Proc. Nat. Acad. Sci.* USA 83:3982–3986; Dautry et al. (1988) *J. Biol. Chem.* 263:17615–17620; and Zmuidzinas et al. (1991) *Mol. Cell. Biol.* 11:2794–2803). By comparison, in the case of the c-myb gene, the induction is unique to the IL-2 signalling pathway (Stern et al. (1986) *Science* 233:203–206). Therefore, to categorize the novel IL-2-induced genes with regard to their patterns of induction by these two receptor pathways, the sensitivity of the genes to T-cell receptor stimulation can be determined.

Additional methods that can be used to categorize the genes isolated include screening for expression by proliferating versus non-proliferating cells, for tissue-specific expression, and for expression in response to different cytokines and hormones. Genes that are expressed exclusively by proliferating cells are obvious candidates for functioning to promote cell growth. Other genes may be important for signaling differentiation and would be expected to be tissue-specific or activated only by a restricted family of similar ligands.

An additional means of elucidating the mechanisms of IL-2-mediated transmembrane signalling is provided by the varied effects of elevated cAMP on IL-2-induced gene expression. The diverse responses of the genes to cAMP suggest that the IL-2 signalling pathways responsible for their induction must bifurcate at a point prior to intersection with the cAMP regulated pathways. One potential mechanism of cAMP action may involve regulation of protein phosphorylation, as cAMP is an activator of protein kinase A, and elevations of intracellular cAMP inhibit IL-2-inducted phosphorylation events. In addition, as cAMP blocks IL-2-stimulated cell cycle progression at a point in early $G_1$, cAMP sensitivity is a useful tool with which to dissect IL-2-mediated signal transduction pathways involved in cell cycle progression.

A likely function of the immediate/early gene products is the governing of subsequent DNA replication and cell division. Previously characterized IL-2 induced genes encode kinases (c-raf-1, pim-1) and DNA binding proteins (c-fos, c-myc, c-myb). Further sequence analysis of the novel genes will determine whether the proteins they encode contain conserved domains which would implicate similar functions. However, since IL-2 stimulates cellular differentiation as well as division, and has been shown to induce the expression of a number of genes which do not per se perform a direct role in cell cycle progression, a functional correlation between the expression of the novel genes and cell cycle transit should be demonstration.

Indirectly, cAMP sensitivity is suggestive of involvement in $G_1$ progression. The demonstration of induction of the genes by other growth factors, as well as heightened expression in transformed cell lines would further support this notion. A more direct approach, utilizing antisense oligonucleotides, will make it possible to determine whether specific blockage of expression of any of these genes is sufficient to prevent cell cycle progression. Similarly, it will be possible to determine whether the immediate early gene products exert cell cycle control through the induction of expression of late genes, as has been demonstrated for regulation of the PCNA/cyclin, DNA polymerase a and cdc2 genes by the c-myb and c-myc gene products. Interestingly, the IL-2-induced expression of the PCNA/cyclin and DNA topoisomerase II gene in late $G_1$ is specifically inhibited by cAMP, so that cAMP sensitivity of immediate early gene expression may provide a useful indicator of which genes play a role in regulating late gene expression. If, like the previously characterized cell cycle regulatory cdc2/CDC28 and cyclin genes, the novel IL-2 induced genes are highly conserved, then it may ultimately be possible to isolate yeast homologs of the clones and perform deletional analyses to further define the functions of the gene products.

Ultimately, the definitive assignment of a given gene product to a particular function within a cell depends upon a series of different approaches, including determining intracellular location, and determining the consequences of blocking the expression of the gene either by mRNA antisense methods or by homologous recombination methods.

All of the methods necessary for these studies exist as prior art and therefore, given the identification of a given gene as activated by a ligand such as the cytokine IL-2 is possible to characterize each gene product.

The invention is illustrated further by the following exemplification which is not meant to limit the scope of the invention, since alternative methods may be used to obtain similar results.

EXAMPLES

1. Cell Culture

Human peripheral blood mononuclear cells (PBMCs) were isolated by Ficoll/Hypaque discontinuous centrifugation, and cultured at $10^6$ cells/ml in complete medium comprised of RPMI 1640 (GIBCO Laboratories, Grand Island, N.Y.) supplemented with 10% heat-inactivated (56° C., 30 min) calf serum (Sterile Systems, Inc., Logan, Utah), 50 mg/ml L-glutamine, and 50 units/ml penicillin. T-cells were activated by stimulation of the CD3 component of the T-cell receptor complex with an anti-CD3 reactive monoclonal antibody (OKT3, 1:10,000 dilution, Ortho Pharmaceuticals, Raritan, N.J.) in the presence of absence of 10 µg/ml CHX, and DNA synthesis was monitored at 48–52 hr by adding 0.5 µCi [$^3$H]-thymidine to 200 µl aliquots of cell cultures in 96-well microtiter plates. Cultures were harvested onto glass fiber filters, radioactivity was counted by liquid scintillation, and [$^3$H]-thymidine incorporation was calculated as cpm/$10^4$ cells/hr.

IL-2R-positive T-cell blasts were prepared by stimulation of PBMCs with OKT3 for 3 days, after which the cells were washed and replaced in culture for an additional 11 days in the presence of 500 pM IL-2. The cells were subsequently washed and placed in culture in the absence of IL-2 for 36 hr, followed by a 12 hr stimulation with 50 ng/ml phorbal 12,13 dibutyrate (PdBu) to augment high-affinity IL-2R expression. Cells were washed free of PdBU and placed in culture for 12 hr prior to restimulation. Such treatment enabled the generation of a $G_0/G_1$-synchronized cell population, made up of greater than 90% T8-positive T lymphocytes (Gullberg et al. (1986) *J. Exp. Med.* 163:270–284).

2. cDNA Library Construction

Human :IL-2R-positive T-cell blasts were cultured in the presence of 1 nM IL-2, 10 mg/ml CHX, 250 µM 4-thiouridine (Sigma Chemical Co., St. Louis, Mo.) and 2.5 µCi/ml [5,6-$^3$H]-uridine (48 Ci/mmole, Amersham, Arlington Heights, Ill.) for 2 hr. CHX was included in the 2 hr IL-2 stimulation of the IL-2R-positive, $G_0/G_1$-synchronized human T-cells from which the cDNA library was generated in order to isolate immediate-early genes, and also to possibly superinduce the expression of low-abundance messages. Total RNA was isolated essentially as described by Caligiuri et al. (*J. Exp. Med.* (1989) 171:1509–1526), and the 4-thiouridine-labelled RNA purified by passage over a phenylmercury agarose column as described by Woodford et al. (*Anal. Biochem.* (1988) 171:166–172). The cells were labelled with 4-thiouridine during stimulation, to enable isolation of only those transcripts which were synthesized during the period of IL-2 and CHX treatment (Stetler et al. *Proc. Nat. Acad. Sci.* (USA), (1984) 81:1144–1148) and Woodford et al. (*Anal. Biochem.* (1988) 171:166–172). Fractionation of total cellular RNA resulted in a 10-fold enrichment for newly-synthesized transcripts.

This thiol-selected RNA was used in the synthesis of Not-1 primer/adaptor-primed cDNA, utilizing the Riboclone cDNA Synthesis System (Promega, Madison, Wis.) according to manufacturers instructions. After addition of EcoRI adaptors (Promega), Not-1 digestion, and size selection for fragments greater than 500 base pairs (bp), the cDNA was ligated directionally into an EcoRI- and Not-1-digested pBluescript II SK+ plasmid vector (Stratagene, La Jolla, Calif.), followed by transformation into Epicurian Coli XL-1 Blue competent cells (Stratagene). A cDNA library of approximately 10,000 clones resulted.

3. Colony Screening

About 10% of the library was then screened using radiolabelled cDNA probes made from mRNA isolated from T-cells induced with IL-2 or from uninduced cells as follows. Single-stranded [$^{32}$P]-labelled cDNA probes were prepared from poly(A)$^+$RNA isolated from human T-cell blasts stimulated for 2 hr with medium (unstimulated probe), or 1 nM IL-2 and 10 µg/ml CHX (stimulated probe). Total cellular RNA was prepared as described by Caligiuri et al. (*J. Exp. Med.* (1989) 171:1509–1526), and poly(A)$^+$RNA was isolated by three passages over an oligo-dT-cellulose column (5 Prime-3 Prime, West Chester, Pa.). First strand cDNA synthesis was performed with an oligo-dT 12–18 primer (United States Biochemical Corp., Cleveland, Ohio), using the Riboclone cDNA Synthesis System (Promega, Madison, Wis.) according to manufacturers instructions, with the exception of dCTP at a final concentration of 35 µM and the addition of 2.5 mCi/ml [$^{32}$P]-dCTP. Hybridization was carried out for 72–96 hr at 42° C. in 50% formamide, with a final probe concentration of approximately $2 \times 10^6$ cpm/ml (W. M. Strauss, in *Current Protocols in Molecular Biology*, (1989) pp. 6.3.1–6.3.6). Subsequent to hybridization, filters were washed repeatedly at 62° C. in 0.1×SSC (1×SSC=0.15M NaCl, 0.015M sodium citrate, pH 7.0), 0.1% SDS and placed on film (Kodak XAR-5) with Dupont Cronex intensifying screens overnight at −70° C. The initial screening yielded 18 putative positive clones which exhibited differential hybridization to the stimulated and unstimulated probes after three independent screens. These clones were isolated for further characterization by Northern Blot analysis.

4. Northern Blot Analysis

Total cellular RNA was isolated by the guanidine thiocyanate method described by Caligiuri et al. (ibid.), and denatured in glyoxal and DMSO. The RNA was fractionated on a 1% agarose gel in 0.01 M NaH$_2$PO$_4$ with 0.5 mg/ml ethidium bromide (Selden, *Current Protocols in Molecular Biology*, (1989) pp. 4.9.5–4.9.8). To estimate sizes of RNA transcripts, a 0.24–9.5 kb RNA ladder (Bethesda Research Laboratories, Gaithersburg, Md.) was run alongside the cellular RNA samples. After visualization under ultraviolet light, the RNA was transferred to nitrocellulose by capillary transfer in 10×SSC. Plasmids were purified from the clones of interest, and the Not-1- and EcoRI-excised inserts [$^{32}$P] -labelled with random primers. Hybridization was carried out in 50% formamide at 42° C. for 48–72 hr, followed by repeated washes in 0.1×SSC, 0.1% SDS at 56–62° C. (Selden, ibid.). Filters were exposed to Kodak XAR-5 film with Dupont Cronex intensifying screens, and specific bands quantitated with an EC densitometer (EC Apparatus Corp., St. Petersburg, Fla.).

In as much as CHX was included in both the library and probe preparation, it was essential to verify that the differential expression of putative clones observed upon colony screening was not due solely to the effects of this drug. In addition, determination of the sizes and patterns of induction of the RNA transcripts was necessary to enable estimation of the redundancy of the clones. Therefore, Northern blot analysis was performed with RNA isolated from human IL-2R-positive T-cell blasts stimulated with either CHX or IL-2 alone, or with a combination of the two agents.

Hybridization of the RNA with probes generated from the inserts of each of the 18 putative clones resulted in the identification of 4 clones that were solely CHX-induced. For the remaining 14 clones, the induction by the combination of IL-2 and CHX could not be accounted for by the effects of CHX alone. Based upon the patterns of induction and approximate sizes of the RNA transcripts, 8 readily distinguishable and apparently unique IL-2-induced genes were discerned among these 14. These are described in TABLE 1.

TABLE 1

| Clone | SEQ ID NO: | Insert (kb) | RNA (kb) | IL-2 Induction |
|---|---|---|---|---|
| 1A8 | 1 | 1.6 | 2.4 | 24 |
| 1F5 | 2, 3 | 1.1 | 0.6, 1.1 | 7 |
| 10A8 | 4, 5 | 2.0 | 2.2, 3.2 | 22 |
| 10D6 | 6, 7 | 1.0 | 3.5 | 6 |
| 10F9 | 8, 9 | 1.4 | 1.7 | >50 |
| 11B2 | 10, 11 | 1.0 | 1.5 | 5 |
| 11E6 | 20 | 0.7 | 2.4 | 17 |
| 13E2 | 19 | 1.5 | 2.8 | 7 |

As shown in this Table and in FIG. 1, three of the genes, 1A8 (SEQ ID NO:1), 10A8 (SEQ ID NOS:4 and 5), and 10F9 (SEQ ID NOS:8 and 9), were induced by IL-2 alone, while five of the genes, 1F5 (SEQ ID NOS:2 and 3), 10D6 (SEQ ID NOS:6 and 7), 11B2 (SEQ ID NOS:10 and 11), 11E6 (SEQ ID NO:20), and 13E2 (SEQ ID NO:19), were induced by both CHX and IL-2. In several instances, the combination of IL-2 and CHX resulted in a marked synergistic induction.

5. Kinetic Analysis of IL-2-Induced Gene Expression

The temporal expression of the novel, IL-2-induced genes was determined by Northern blot analysis, using RNA isolated from human IL-2R-positive T-cell blasts after IL-2 stimulation in the presence or absence of CHX. Northern blots were prepared with 15 µg total RNA isolated from G$_0$/G$_1$-synchronized human T-cells stimulated for 0, 0.5, 1, 2, 4, or 8 hours with 1 nM IL-2 or IL-2+10 µg/ml CHX. Filters were probed with the cDNA inserts of the IL-2-induced clones.

As shown in FIGS. 5A–5H, two of the genes, 1A8 (SEQ ID NO:1) (FIG. 5A) and 10D6 (SEQ ID NOS:6 and 7) (FIG. 5B), exhibited rapid induction, reaching peak levels within 1–4 hr of IL-2 stimulation and returning to basal levels after 8 hr, while the other six clones (FIGS. 5C–5H) remained at elevated levels for at least 8 hr after IL-2 treatment. The magnitude of IL-2 induction of steady state RNA levels of the clones ranged from an approximately 5-fold elevation of clone IIB2 (SEQ ID NOS:10 and 11) (FIG. 5F) to a greater than 50-fold stimulation of clone 10F9 (SEQ ID NOS:8 and 9) (FIG. 5E) during the interval examined. These results are also summarized in TABLE 1. Several of the clones were superinduced by CHX, with an increase observed in both the magnitude and duration of the IL-2 response.

The kinetics of induction of previously characterized IL-2-responsive genes have been found to range from those such as c-fos, which are rapidly and transiently induced within minutes of IL-2 stimulation (Dautry et al. (1988) *J. Biol. Chem.* 263:17615–17620), to those which remain at elevated levels through G1 to S phase entry (Sabath et al. (1990) *J. Biol. Chem.* 265:12671–12678).

6. Sequence Analysis

To verify the redundancy of the clones as estimated from Northern analysis, as well as to determine the identities of the genes, the cDNA clones were subjected to sequence analysis.

Plasmids were isolated from the clones of interest essentially as described by Kraft et al. (*BioTechniques* (1988)

6:544–547), and vector primers were used to sequence the termini of the cDNA inserts, employing the Sequenase 2.0 dideoxy sequencing kit (United States Biochemical, Cleveland, Ohio). Approximately 200 bases of sequence were attained from each end of the inserts. These partial sequences are set forth in the Sequence Listing as SEQ ID NOS: 1–19. Searches of the GenBank and EMBL data bases were performed with the FASTA program as described by Pearson et al. (*Proc. Natl. Acad. Sci.* (USA) (1988) 85:2444–2448).

The combination of sequence and Northern analyses revealed that the 14 putative IL-2-induced clones consisted of 8 unique genes, three of which, (1A8 (SEQ ID NO:1), 11B2 (SEQ ID NOS:10 and 11), and 13E2 (SEQ ID NO:15), were isolated three times each. Searches of the GenBank and EMBL data bases with the partial sequences enabled the identification of one clone, 11E6 (SEQ ID NO:20), as pim-1, a previously characterized IL-2-induced gene (Dautry et al. (1988) *J. Biol. Chem.* 263:17615–17620; and Kakut-Hour i et al. (1987) Gene 54:105–111) which encodes a 33 kD cytoplasmic kinase (Telerman et al. (1988) *Mol. Cell. Biol.* 8:1498–1503). The others did not show significant homology to any known sequences.

Thus, by utilizing the method of the invention seven unique IL-2 induced genes were cloned, representing novel human genes. These clones were identified after screening only approximately 800 library colonies, and thus, it is estimated that as many as 80 additional novel IL-2-induced genes remain to be detected in the 10,000-clone library.

7. Sensitivity of IL-2-Induced Gene Expression

As a further means of characterizing the regulation of expression of these genes, the sensitivity of induction to the known IL-2 functional antagonist was investigated. Human IL-2R-positive T-cell blasts were stimulated with IL-2 in the absence or presence of 0.5 mM dibutyryl-cAMP, a concentration of the membrane-permeant cAMP analog sufficient to inhibit IL-2-mediated $G_1$ progression without adversely affecting cellular viability. The effect of an equivalent molar amount of sodium butyrate, which does not inhibit the IL-2 response, was also tested to control for the actions of free butyric acid.

Northern blots were prepared as follows: Human IL-2R-positive T cells were treated with 1 nM IL-2 alone or in combination with 0.5 mM dibutyryl cAMP or sodium butyrate (NaBt) for 1, 2, or 4 hours. Filters were prepared with 15 µg total RNA and hybridized with cDNA inserts or the IL-2 induced clones.

These analyses demonstrate that the IL-2 induction of one gene, 1A8 (SEQ ID NO:1) (FIG. 2A) is markedly inhibited when the intracellular level of cAMP is raised by the addition of dibutyryl cAMP, whereas the expression of two others, 10D6 (SEQ ID NOS:6 and 7) (FIG. 2A) and 13E2 (SEQ ID NO:15) (FIG. 2C), is augmented approximately 3-fold. By comparison, the expression of five of the genes was not affected by elevated cAMP (FIGS. 2D–2H). Thus, the sequences in clone 1A8 (SEQ ID NO:1) may be involved in T-cell proliferation. The fact that not all genes were sensitive to cAMP indicated that the observed results were not due to non-specific effects, and furthermore that the previously documented down-regulation of IL-2R binding capacity by cAMP (Johnson et al. (1990) *J. Immunol.* 145:1144–1151) could not account for the inhibition of gene expression.

8. Responsive To T-cell Receptor Stimulation

In order to determine if activation of the T-cell receptor mediates the stimulation of expression of cytokine IL-2-induced genes, the following study was performed. Northern blots were prepared from 20 µg total cellular RNA isolated from human peripheral blood mononuclear cells (PBMCs) stimulated with a monoclonal antibody (OKT3) specific to the CD3 component of the T-cell antigen receptor complex. Blots were probed with cDNA inserts of the IL-2-induced clones. Data was determined as the mean ±SEM (n=6).

By isolation of RNA at early time intervals, it was possible to identify those genes which were induced by T-cell receptor triggering in the absence of IL-2 effects. As shown in FIGS. 3A–3H, only one of the genes, 10D6 (SEQ ID NOS:6 and 7) exhibited heightened levels of expression after 2 hr of T-cell receptor activation, while the seven others were apparently insensitive to this stimulus. Two of the clones, 1F5 (SEQ ID NOS:2 and 3) and 11B2 (SEQ ID NOS:10 and 11), were undetectable, even after seven days of autoradiographic exposure of the Northern blots. Two other genes, 11E6 (SEQ ID NO:20) and 13E2 (SEQ ID NO:15), were expressed at relatively high levels regardless of the stimulus; activation with anti-CD3 did not induce RNA expression beyond the level observed by culture in medium alone. Identical results were obtained after 1 and 4 hr of stimulation.

To determine whether the cells were actually activated via CD3, aliquots of the cells were left in culture for 52 hr in the presence of 10 µg/ml CHX, alone, OKT3 alone, or OKT3 +CHX, after which cell cycle progression was monitored by [$^3$H]-thymidine incorporation into RNA.

Figure 4:
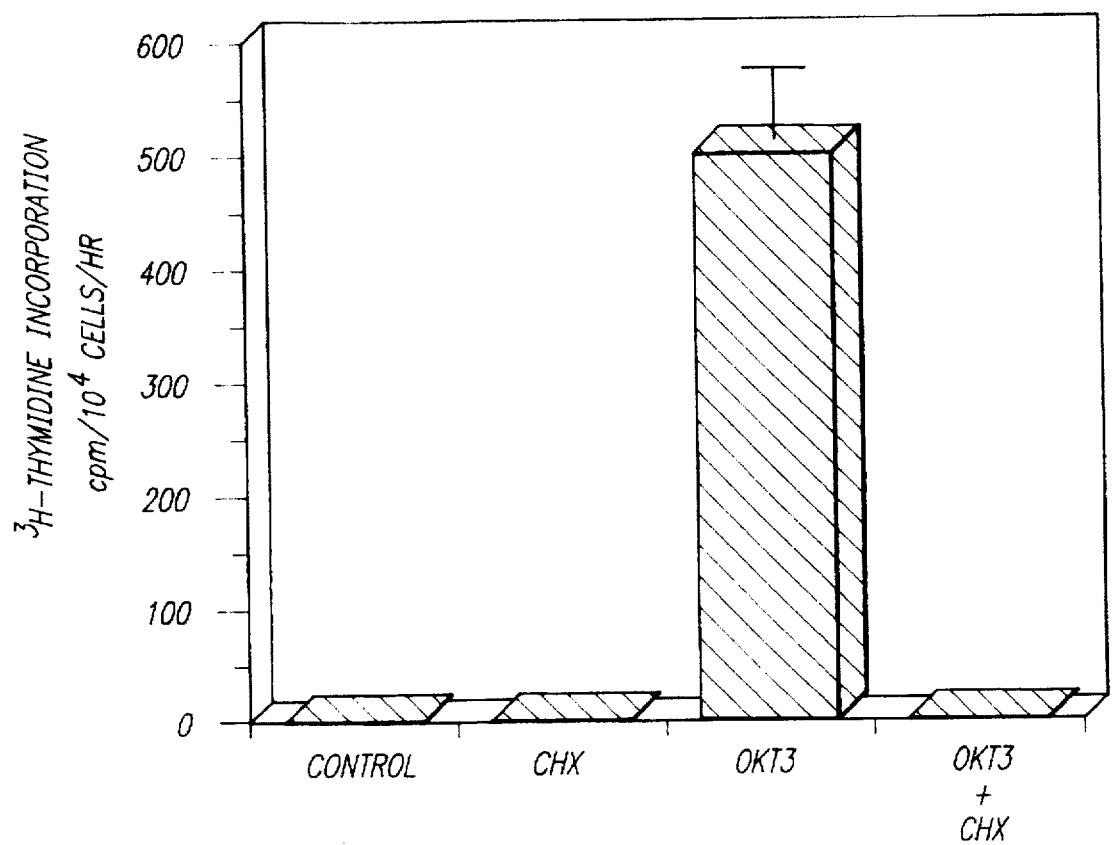
FIG. 4 is a histogram showing the level of DNA synthesis (as the incorporation of [$^3$H]-thymidine in PBMN cells treated with CHX, OKT3 or OKT3 and CHX.
Figure 5:
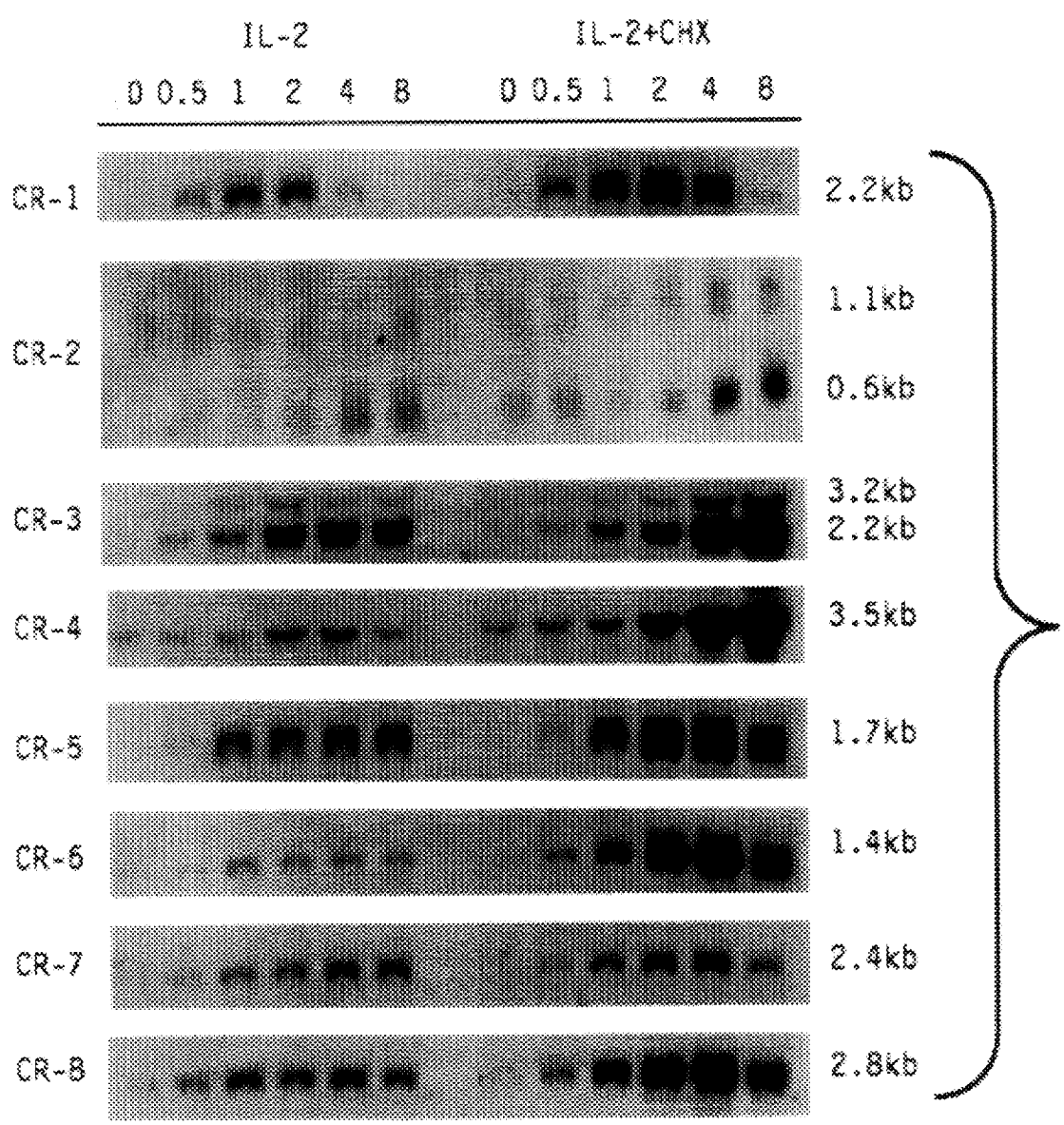
FIG. 5A–5H are photographic representations of Northern blots showing the kinetics of IL-2-induced gene expression. RNA from unstimulated, IL-2-stimulated, or IL-2+10 µg/ml CHX-stimulated cells was probed with cDNA inserts of the following IL-2-induced clones.

As shown in FIG. 4, the cells were sufficiently stimulated by anti-CD3. Thus, the T-cell receptor-induced expression of only one of the genes was comparable to that seen with IL-2 stimulation, while the expression of the seven others was unique to the IL-2 signaling pathway.

Thus, the methods described herein to identify IL-2-induced gene successfully selected and enriched for these genes that are highly specific for cytokine (IL-2) activation.

Of the 8 IL-2 induced $G_1$ progression genes reported here, only one appears to also be induced during the T cell receptor-mediated competence phase of the cell cycle. Thus, while several genes such as c-fos, c-myc and c-raf-1 are known to be induced during both the initial $G_0$–$G_1$ and subsequent $G_1$-S phase transitions, the expression of a number of IL-2-stimulated genes is unique to the latter event. In addition, the immediate-early genes reported here appear to define a class distinct from the IL-2-induced genes isolated by Sabath et al. (*J. Biol. Chem.* (1990) 265:12671–12678). These investigators utilized a differential screening procedure to isolate genes expressed at the $G_1$/S phase boundary in a murine T helper clone which was stimulated with IL-2 for 20 hr in the absence of protein synthesis inhibitors. In this case, the expression of only 3 of the 21 clones isolated was inhibited by CHX, while the remainder were insensitive to this agent. This pattern of regulation markedly contrasts with the CHX superinduction observed with the immediate-early IL-2-induced genes described here. Moreover, these observations indicate that IL-2 stimulates a complex program of gene expression, ranging from those genes induced very early in $G_1$ through those subsequently expressed at the $G_1$/S phase transition.

EQUIVALENTS

Those skilled in the art will recognize, or be able to ascertain using no more than routine experimentation, numerous equivalents to the specific procedures described herein. Such equivalents are considered to be within the scope of this invention, and are covered by the following claims.

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 1562 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 1A8-T7

( x i ) SEQUENCE DESCRIPTION: SEQ ID NO:1:

```
TGCGCTCCAG CAGCCTGTTT GGGAAGCAGC AGTCTCTCCT              40
TCAGATACTG TGGGACTCAT GCTGGAGAGG AGCCGCCCAC              80
TTCCAGGACC TGTGAATAAG GGCTAATGAT GAGGGTTGGT             120
GGGGCTCTCT GTGGGGCAAA AAGGTGGTAT GGGGGTTAGC             160
ACTGGCTCTC GTTCTCACCG GAGAAGGAAG TGTTCTAGTG             200
TGGTTTAGGA AACATGTGGA TAAAGGGAAC CATGAAAATG             240
AGAGGAGGAA AGACATCCAG ATCAGCTGTT TTGCCTGTTG             280
CTCAGTTGAC TCTGATTGCA TCCTGTTTTC CTAATTCCCA             320
GACTGTTCTG GGCACGGAAG GGACCCTGGA TGTGGAGTCT             360
TCCCCTTTGG CCCTCCTCAC TGGCCTCTGG GCTAGCCAGA             400
GTCCCTTAGC TTGTACCTCG TAACACTCCT GTGTGTCTGT             440
CCAGCCTTGC AGTCATGTCA AGGCCAGCAA GCTGATGTGA             480
CTCTGCCATG CGAGATATTA TACCTCAAAC ACTGGCCTGT             520
GAGCCCTTTC CAAGTCAGTG GAGAGCCCTG AAAGGAGCCT             560
CACTTGAATC CAGCTCAGTG CTCTGGGTGG CCCCCTGCAG             600
GTGGCCCCTG ACCCTGCGTT GCAGCAGGGT CCACCTGTGA             640
GCAGGCCCGC CCTGGGGCCT CTTCCTGGAT GTGCCCTCTC             680
TGAGTTCTGT GCTGTCTCTT GGAGGCAGGG CCCAGGAGAA             720
CAAAGTGTGG AGGCCTCGGG GAGTGGCTTT TCCAGCTCTC             760
ATGCCCCGCA GTGTGGAACA AGGCAGAAAA GGATCCTAGG             800
AAATAAGTCT CTTGGCGGTC CCTGAGAGTC CTGCTGAAAT             840
CCAGCCAGTG TTTTTGTGG TATGAGAACA GGCAAAAAGA              880
GATGCCCCGA GATAGAAGGG GAGCCTTGTG TTTCTTTCCT             920
GCAGACGTGA GATGAACACT GGAGTGGGCA GAGGTGGCCC             960
```

| | |
|---|---|
| AGGACCATGC ACCTTAGAGT GCAGAGCTGG GGGGAGAGGC | 1000 |
| TGCTTCGAAG GGCAGGACTG GGGATAATCA GAACCTGCCT | 1040 |
| GTCACCTCAG GGCATCACTG AACAAACATT TCCTGATGGG | 1080 |
| AACTCCTGCG CAGAGCCCAG GCTGGGGAAG TGAACTACCC | 1120 |
| AGGGCAGCCC CTTTGTGGCC CAGGATAATC AACACTGTTC | 1160 |
| TCTCTGTACC ATGAGCTCCT CCAGGAGATT ATTTAAGTGT | 1200 |
| ATTGTATCAT TGGTTTTCTG TGATTGTCAT AACATTGTTT | 1240 |
| TTGTTATTGT TGGTGCTGTT GTTATTTATT ATTGTAATTT | 1280 |
| CAGTTTGCCT CTACTGGAGA ATCTCAGCAG GGGTTTCAGC | 1320 |
| CTGACTGTCT CCCTTTCTCT ACCAGACTCT ACCTCTGAAT | 1360 |
| GTGCTGGGAA CCTCTTGGAG CCTGTCAGGA ACTCCTCACT | 1400 |
| GTTAAATAT TTATTTATTG TGACAAATGG AGCTGGTTTC | 1440 |
| CTAGATATGA ATGATGTTTG CAATCCCCAT TTTCCTGTTT | 1480 |
| CAGCATGTTA TATTCTTATA AATAAAAGC AAAAGTCAAA | 1520 |
| TATGAAAAAA AAAAAAAAA AAAAAAAAA AAAAAAAA | 1560 |
| AA | 1562 |

( 2 ) INFORMATION FOR SEQ ID NO:2:

( i ) SEQUENCE CHARACTERISTICS:
        ( A ) LENGTH: 188 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 1F5

( x i ) SEQUENCE DESCRIPTION: SEQ ID NO:2:

| | |
|---|---|
| TATTAGACCT CTCAGGTAGC AGCTGAGACA TTGTATCCAG | 40 |
| TTTCCTGATT GTTTTCAATG GAATAATCAT GTATACATGC | 80 |
| ACTACTAATG AGACAATGGT GATTCTAAAA GCTTAATCAG | 120 |
| GGGGACTTTT GTGTATTCCA AATCTACTAA AAATAAAGAA | 160 |
| ACACAGAAAT GAGAAAAAAA AAAAAAA | 188 |

( 2 ) INFORMATION FOR SEQ ID NO:3:

( i ) SEQUENCE CHARACTERISTICS:
        ( A ) LENGTH: 163 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
    ( A ) ORGANISM: human
    ( G ) CELL TYPE: T-cell blast ( v i i ) IMMEDIATE SOURCE:
    ( A ) LIBRARY:
    ( B ) CLONE: 1F5-T7

( x i ) SEQUENCE DESCRIPTION: SEQ ID NO:3:

```
ATTTAGAGCA  ACTCAGGAAA  TAGGTGCACA  CAAGCAAACC                40

ATGTGGTTAA  AGCCTTTGGA  ACTGGTTTGA  GCAAAGCTGT                80

AGGTGATTTG  ACAAAATCAT  CTGCAAAACC  AGATTTCTAA               120

CACTCCTGCT  GTGTATCTCA  TTCTGCTGAT  GTGTGTGCTC               160

ATA                                                          163
```

( 2 ) INFORMATION FOR SEQ ID NO:4:

( i ) SEQUENCE CHARACTERISTICS:
        ( A ) LENGTH: 199 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 10A8

( x i ) SEQUENCE DESCRIPTION: SEQ ID NO:4:

```
GTTTGACTCA  TCTTATATGG  GAAACCATGT  AGCAGTGAGT                40

CATATCTTAA  TATATTTCTA  AATGTTTGGC  ATGTAAACGT                80

AAACTCAGCA  TNAAAATATT  TCAGTGAATT  TGCACTGTTT               120

AATCATAGTT  ACTGTGTAAA  CTCATCTGAA  ATGTTACAAA               160

AATAAACTAT  AAAACAAAAA  TTTGAAAAAA  AAAAAAAA                 199
```

( 2 ) INFORMATION FOR SEQ ID NO:5:

( i ) SEQUENCE CHARACTERISTICS:
        ( A ) LENGTH: 182 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 10A8-T7

( x i ) SEQUENCE DESCRIPTION: SEQ ID NO:5:

| | | | | |
|---|---|---|---|---|
| TCTCCCTGCT | CTTCTGCTCG | CTGCCGCTGC | TGGACTATGG | 40 |
| GCAGTACGTC | CAGTACTGCC | GGGACCTGGT | GCTTCATCCG | 80 |
| GCACGGCGGA | CCGCTTACCT | GCAGCTGTAC | GCCACCCTGC | 120 |
| TGCTGCTTCT | CATTGTCTCG | GTGCTCGCCT | GCAACTTCAG | 160 |
| TGTCATTCTC | AACTCATCCG | CA | | 182 |

( 2 ) INFORMATION FOR SEQ ID NO:6:

( i ) SEQUENCE CHARACTERISTICS:
        ( A ) LENGTH: 249 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 10D6

( x i ) SEQUENCE DESCRIPTION: SEQ ID NO:6:

| | | | | |
|---|---|---|---|---|
| TTCCTCTGTT | TTACAAACTG | CTTGGCAGCC | CCAGGTGAAG | 40 |
| CATCAAGGAT | TGTTTGGTAT | TAAAATTTGT | GTTCACGGGA | 80 |
| TGCACCAAAG | TGTGTACCCC | GTAAGCATGA | AACCAGTGTT | 120 |
| TTTGTTTTT | TTTTAGTTC | TTATTCCGGA | GCCTCAAACA | 160 |
| AGCATTATAC | CTTCTGTGAT | TATGATTTCC | TCTCCTATAA | 200 |
| TTATTTCTGT | AGCACTCCAC | ACTGATCTTT | GGAAACTTGC | 240 |
| CCCTTATTT | | | | 249 |

( 2 ) INFORMATION FOR SEQ ID NO:7:

( i ) SEQUENCE CHARACTERISTICS:
        ( A ) LENGTH: 201 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 10D6-T7

( x i ) SEQUENCE DESCRIPTION: SEQ ID NO:7:

| | | | | |
|---|---|---|---|---|
| CCGTTGCTGT | CGCACGGTGG | CCTCTCCAGC | AGAGTCAGAT | 40 |
| GAGGAAAACC | GACAGAAGAC | CCGGCCACGA | ACAAAAATTT | 80 |

-continued

| | | | | |
|---|---|---|---|---|
| CAGTGGAAGC | CTTGGGAATC | CTCCAGAGTT | TCATACAAGA | 120 |
| CGTGGGCCTG | TACCCTGACG | AAGAGGCCAT | CCAGACTCTG | 160 |
| TCTGCCCAGC | TCGACCTTCC | CAAGTNNCAT | CATCAAGTTC | 200 |
| T | | | | 201 |

( 2 ) INFORMATION FOR SEQ ID NO:8:

( i ) SEQUENCE CHARACTERISTICS:
        ( A ) LENGTH: 397 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 10F9-T3

( x i ) SEQUENCE DESCRIPTION: SEQ ID NO:8:

| | | | | |
|---|---|---|---|---|
| ATATTGGAGA | TGACACTACA | TAGTAGAAAT | GCAGCCGGAG | 40 |
| CCTCAGTCCC | CAGCAGAGCC | TGTGTCTCAC | CCCCTCACAG | 80 |
| GACAGAGCTG | TATCTGCATG | AGCTGGTCTC | ACTGTGGCGC | 120 |
| AGGCCCGGGG | GGAGTGCCTT | GGCTGTCAGA | GANNNTGCTG | 160 |
| GTTGAGGCC | ACCACTGCAG | TCTGCTAGGT | CTGCTCCTGC | 200 |
| CCAGGAAGGT | GCCTGCACAT | GAGAGGAGAG | AAATACACGT | 240 |
| CTGATAAGAC | TTCATGAAAT | AATAATTATA | GCAAAGAACA | 280 |
| GTTGGTGGT | CTTTTCTCTT | CCCTGATTTT | TCTGTAATTG | 320 |
| ACATTATACC | TTTATTACCT | CTTTATTTTA | TTACCTCTAT | 360 |
| AATAAAATGA | TACCTTTCAT | GTAAAAAAAA | AAAAAA | 397 |

( 2 ) INFORMATION FOR SEQ ID NO:9:

( i ) SEQUENCE CHARACTERISTICS:
        ( A ) LENGTH: 199 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 10F9-T7

( x i ) SEQUENCE DESCRIPTION: SEQ ID NO:9:

| | | | | |
|---|---|---|---|---|
| TTGCTGTCGG | CAGTGCCCGC | AGCCTGCAAC | ACCTGTGCCG | 40 |

| | | | | |
|---|---|---|---|---|
| CCTTGTCATC | AACCGTCTGG | TGGCCGACGT | GGACTGCCTG | 80 |
| CCACTGCCAC | TGCCCCGGCG | CATGGCCGAC | TACCTCCGAC | 120 |
| AGTACCCCTT | CCAGCTCTGA | CTGTACGGGG | CAATTGCACC | 160 |
| CTCACCCAGT | CGCACCTGGA | GGACATCAGC | CAGCTGACT | 199 |

( 2 ) INFORMATION FOR SEQ ID NO:10:

( i ) SEQUENCE CHARACTERISTICS:
        ( A ) LENGTH: 385 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 11B2

( x i ) SEQUENCE DESCRIPTION: SEQ ID NO:10:

| | | | | |
|---|---|---|---|---|
| CGCTGAACTG | CAGGCGGGGG | GGGCGCCTGA | GAGCGAGAGC | 40 |
| GCGGCTCCCG | AGGAGGGGCC | CGGTGGCGCA | GGGCCAGGCT | 80 |
| GGTCCGAGCT | GAGGACTCTG | CAAGTGTCTG | GAGCGCTGCT | 120 |
| CGCCCAGGAA | GGCCTAGGCT | AGACGTGNNC | TCAGGCNNNN | 160 |
| ANNGACAGAC | TGNNCGGGCA | GGCGTGACTC | AGCAGCTGCG | 200 |
| CTCGGGCAGG | AAAGGCAGGA | AAGGAGCGGC | GCCCTGGACT | 240 |
| TGGTACAGTT | GCAGGAGCGT | GAAGGACTTA | GCCGACTGCG | 280 |
| CTGCTTTTTC | AAAACGGATC | CGGGCAATGC | TTCGTTTTCT | 320 |
| AAAGGATGCT | GCTGTTGAAG | CTTTGAATTT | TACAATAAAC | 360 |
| TTTTTGAAAC | AAAAAAAAAA | AAAAA | | 385 |

( 2 ) INFORMATION FOR SEQ ID NO:11:

( i ) SEQUENCE CHARACTERISTICS:
        ( A ) LENGTH: 204 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 11B2-T7

( x i ) SEQUENCE DESCRIPTION: SEQ ID NO:11:

| | | | | |
|---|---|---|---|---|
| CATCGCGCTG | CAGATCCATT | TTACGCTGAT | CCAGGCTTCT | 40 |

```
GCTGCGAGAA CGACATCGAC ATAGTGCGCG TGGGCGATGT                    80

GCAGCGGCTG GCGGCTATCG TGGNCNGGC GAAGGAGGCG                    120

GGTNNNNCGA CCTGCACTGC ATCCTCATTT CGAACCCAAC                   160

GAGGACNCCT GGAAGATCCC GCCTTGGAGA AGCTCAGCCT                   200

GTTT                                                          204
```

( 2 ) INFORMATION FOR SEQ ID NO:12:

( i ) SEQUENCE CHARACTERISTICS:
        ( A ) LENGTH: 320 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 1G9-T3

( x i ) SEQUENCE DESCRIPTION: SEQ ID NO:12:

```
CCGAGACCTG CATTGTCTCC TGTCACGAAC CCTCACACGG                    40

ACGCCTGGAA GAGCCACGGC TTGGTGGAGG AGGCCAGCTA                    80

CTGCGAAGAA AGCCGGAACA ACCAGTGGGT CCCCTACATC                   120

TCTCTTCAGG AACGCTGAGG CCCTTCCCAG CAGCAGAATC                   160

TGTTGAGTTG CTGCCACAAA GAAAAAATAC AATAAATATT                   200

TGAACCCCCT GGGCCCAGC ACAACCCCCC CAAAACAACC                    240

CAACCCACGA GGACCATCGG GGGCAGAGTC GTTGGAGACT                   280

GAAGAGGAAG AGGAGGAGGA GAAGGGGAGT GAGCGGCCGC                   320
```

( 2 ) INFORMATION FOR SEQ ID NO:13:

( i ) SEQUENCE CHARACTERISTICS:
        ( A ) LENGTH: 227 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 1G9-T7

( x i ) SEQUENCE DESCRIPTION: SEQ ID NO:13:

```
TCGCCCTGCA AATCCACTTC ACGCTCATCC AGTCCTTCTG                    40

CTGTGACAAC GACATCAACA TCGTGCGGGT GTCGGGCATG                    80
```

```
CAGCGCCTGG  CGAGCTCCTG  GGAGAGCCGG  CCGAGACCCA                    120

GGGCACCACC  GAGGCCCGAG  ACCTGCATTG  TCTCCTGGTC                    160

ACGAACCCTC  ACACGGANNC  CTGGAAGAGC  CACGGCTTGG                    200

TGGAGNNNNC  CAGCTACTGC  GAAGAAA                                   227
```

( 2 ) INFORMATION FOR SEQ ID NO:14:

( i ) SEQUENCE CHARACTERISTICS:
        ( A ) LENGTH: 150 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 3B2-T7

( x i ) SEQUENCE DESCRIPTION: SEQ ID NO:14:

```
CCGTTGCTGT  CGCCAGCATC  ACCCTCCCCG  AGTGACAGCC                    40

CGGCGGGACC  TTGGTCTGAT  CGACGTGGTG  ACGCCCGGG                     80

GCCTAGAGCG  GGCTGGCTCT  GTGGAGGGGC  CCTCCGAGGG                    120

TGCCGAGTGC  GGCGTGGAGA  CTGGCAGGCG                                150
```

( 2 ) INFORMATION FOR SEQ ID NO:15:

( i ) SEQUENCE CHARACTERISTICS:
        ( A ) LENGTH: 184 base pairs
        ( B ) TYPE: nucleic acid
        ( C ) STRANDEDNESS: single stranded
        ( D ) TOPOLOGY: linear ( i i ) MOLECULE TYPE: cDNA ( i i i ) HYPOTHETICAL: no ( i v ) ANTI-SENSE: no ( v i ) ORIGINAL SOURCE:
        ( A ) ORGANISM: human
        ( G ) CELL TYPE: T-cell blast ( v i i ) IMMEDIATE SOURCE:
        ( A ) LIBRARY:
        ( B ) CLONE: 13E2

( x i ) SEQUENCE DESCRIPTION: SEQ ID NO:15:

```
GGAGGGCTGC  GACGCTTGCT  CTGTTTGTGG  GGTGACGGGA                    40

CTCAGGCGGG  ACAGTGCTGC  AGCTCCCTGG  CTTCTGTGGG                    80

NCCCCTCACC  TACTTACCCA  GGTGGGTCCC  GGCTCTGTGG                    120

GTGATGGGGA  GGGGCATTGC  TGACTGTGTA  TATAGGATAA                    160

TTATGAAAAG  CAGTTCTGGA  TGGT                                      184
```

( 2 ) INFORMATION FOR SEQ ID NO:16:

( i ) SEQUENCE CHARACTERISTICS:

(A) LENGTH: 198 base pairs
(B) TYPE: nucleic acid
(C) STRANDEDNESS: single stranded
(D) TOPOLOGY: linear (ii) MOLECULE TYPE: cDNA (iii) HYPOTHETICAL: no (iv) ANTI-SENSE: no (vi) ORIGINAL SOURCE:
(A) ORGANISM: human
(G) CELL TYPE: T-cell blast (vii) IMMEDIATE SOURCE:
(A) LIBRARY:
(B) CLONE: 8D4-T3

(xi) SEQUENCE DESCRIPTION: SEQ ID NO:16:

| | | | | |
|---|---|---|---|---|
| CCGAGCAGCT | TTTCAAAATG | CACTATGCCT | GATTGCTGAT | 40 |
| CGTGTTTTAA | CTTTTTCTTT | TCCTGTTTTT | ATTTTGGTAT | 80 |
| TAAGTCGTTG | CCTTTATTTG | TAAAGCTGTT | ATAAATATAT | 120 |
| ATTATATAAA | TATATTAAAA | AGGAAAATGT | TTCAGAAAAA | 160 |
| AAAAAAAAAA | AAAAAAAAAA | AAAAAAAAAA | AAAAAAA | 198 |

(2) INFORMATION FOR SEQ ID NO:17:

(i) SEQUENCE CHARACTERISTICS:
(A) LENGTH: 173 base pairs
(B) TYPE: nucleic acid
(C) STRANDEDNESS: single stranded
(D) TOPOLOGY: linear (ii) MOLECULE TYPE: cDNA (iii) HYPOTHETICAL: no (iv) ANTI-SENSE: no (vi) ORIGINAL SOURCE:
(A) ORGANISM: human
(G) CELL TYPE: T-cell blast (vii) IMMEDIATE SOURCE:
(A) LIBRARY:
(B) CLONE: 8D4-T7

(xi) SEQUENCE DESCRIPTION: SEQ ID NO:17:

| | | | | |
|---|---|---|---|---|
| GCGTGTTGGT | ATAGGACTTT | AAAGCTCCTT | TTGGCATAGG | 40 |
| GAAGTCACGA | AGGATTGCTT | GACATCAGGA | GACTTGGGGG | 80 |
| GATTGTAGCA | GACGTCTTGG | GCTTTNNNCC | ACCCAGAGAA | 120 |
| TAGCCCCCTT | CGATACACAT | CANTGGATTT | TCAAAANTTC | 160 |
| AAAGTCTTGG | TCT | | | 173 |

(2) INFORMATION FOR SEQ ID NO:18:

(i) SEQUENCE CHARACTERISTICS:
(A) LENGTH: 176 base pairs
(B) TYPE: nucleic acid
(C) STRANDEDNESS: single stranded
(D) TOPOLOGY: linear (ii) MOLECULE TYPE: cDNA (iii) HYPOTHETICAL: no (iv) ANTI-SENSE: no ( v i ) ORIGINAL SOURCE:
(A) ORGANISM: human
(G) CELL TYPE: T-cell blast ( v i i ) IMMEDIATE SOURCE:
(A) LIBRARY:
(B) CLONE: 8G8-T7

( x i ) SEQUENCE DESCRIPTION: SEQ ID NO:18:

| | | | | |
|---|---|---|---|---|
| GCGTGTTGGT | ATAGGACTTT | AAAGCTCCTT | TTGGCATAGG | 40 |
| GAAGTCACGA | AGGATTGCTT | GACATCAGGA | GACTTGGGGG | 80 |
| GGATTGTAGC | AGACGTCTGG | GCTTTNNNCC | CACCCAGAGA | 120 |
| ATANNNCCCT | TCGATACACA | TCAGCTGGAT | TTTCAAAAGC | 160 |
| TTCAAAGTCT | TGGTCT | | | 176 |

( 2 ) INFORMATION FOR SEQ ID NO:19:

( i ) SEQUENCE CHARACTERISTICS:
(A) LENGTH: 194 base pairs
(B) TYPE: nucleic acid
(C) STRANDEDNESS: single stranded
(D) TOPOLOGY: linear ( i i ) MOLECULE TYPE: cDNA ( i i i ) HYPOTHETICAL: no ( i v ) ANTI-SENSE: no ( v i ) ORIGINAL SOURCE:
(A) ORGANISM: human
(G) CELL TYPE: T-cell blast ( v i i ) IMMEDIATE SOURCE:
(A) LIBRARY:
(B) CLONE: 13E2-T7

( x i ) SEQUENCE DESCRIPTION: SEQ ID NO:19:

| | | | | |
|---|---|---|---|---|
| CACGAAGGAT | TGCTTGACAT | CAGGAGACTT | GGGGGGGATT | 40 |
| GTAGCAGACG | TCTGGGCTTT | TCCCCACCCA | GAGAATAGCC | 80 |
| CCCTTCGATA | CACATCAGCT | GGATTTTCAA | AAGCTTCAAA | 120 |
| GTCTTGGTCT | GTGAGTCACT | CTTCAGTTTG | GGAGCTGGGT | 160 |
| CTGTGGCTTG | ATCAGAGTAC | TTCAAAGAGG | CTTC | 194 |

( 2 ) INFORMATION FOR SEQ ID NO:20:

( i ) SEQUENCE CHARACTERISTICS:
(A) LENGTH: 195 base pairs
(B) TYPE: nucleic acid
(C) STRANDEDNESS: single stranded
(D) TOPOLOGY: linear ( i i ) MOLECULE TYPE: cDNA ( i i i ) HYPOTHETICAL: no ( i v ) ANTI-SENSE: no ( v i ) ORIGINAL SOURCE:
(A) ORGANISM: human
(G) CELL TYPE: T-cell blast ( v i i ) IMMEDIATE SOURCE:
(A) LIBRARY:
(B) CLONE: 11E6-T3

( i x ) FEATURE:

-continued

```
( A ) NAME/KEY: pim-1
( C ) IDENTIFICATION METHOD: sequence
              analysis and comparison with published
              sequence ( x ) PUBLICATION INFORMATION:
      ( A ) AUTHORS: Zakut-Houri, R.
                     Huzum, S.
                     Girol, D.
                     Telerman, A.
      ( B ) TITLE: The cDNA Sequence and Gene
                   Analysis of the Human pim
                   Oncogene
      ( C ) JOURNAL: Gene
      ( D ) VOLUME: 54
      ( E ) ISSUE:
      ( F ) PAGES: 105-111
      ( G ) DATE: 1987

( x i ) SEQUENCE DESCRIPTION: SEQ ID NO:20:
```

| | | | | |
|---|---|---|---|---|
| ATTGCTGACT | GTGTATATAG | GATAATTATG | AAAAGCAGTT | 40 |
| CTGGATGGTG | TGCCTTCCAG | ATCCTCTCTG | GGGNTGTGTT | 80 |
| TTGAGCAGCA | GGTAGCCTGC | TGGTTTATC | TGAGTGAAAT | 120 |
| ACTGTACAGG | GGNATAAAAG | AGATCTTATT | TTTTTTTTA | 160 |
| TACTTGGCGT | TTTTGAATA | AAAACCTTTT | GTCTT | 195 |

I claim:

1. A method of producing a superinduced complementary DNA (cDNA) library enriched in ligand-inducible genes of a cell, comprising the steps of:
   (a) activating a cellular ligand receptor of a cell for a predetermined period of time in the presence of
       thiol-labeled RNA precursors which are incorporated into the RNA synthesized by said cell in response to receptor activation and
       a substance which enhances the level of RNA in said cell;
   (b) separating the thiol-labeled RNA from the remaining RNA;
   (c) preparing cDNA from said labeled RNA, and selecting fragments greater than 500 bp; and
   (d) cloning said selected cDNA in host cells to obtain a library of cDNA-containing clones.

2. The method of claim 1 wherein step (a) comprises exposing said cell to a ligand which binds to said receptor, said ligand being at a level effective to activate said receptor.

3. The method of claim 2 wherein step (a) comprises activating said receptor by exposing said cell to a ligand selected from the group consisting of cytokines, antibodies, peptides, and receptor-binding fragments thereof.

4. The method of claim 3 wherein step (a) comprises treating said cell with a cytokine selected from the group consisting of the interleukins, cellular growth factors, colony stimulating factors, and hormones.

5. The method of claim 4 wherein said cytokine is interleukin-2 (IL-2).

6. The method of claim 1 wherein step (a) comprises activating said receptor in the presence of radiolabelled nucleoside 5'-triphosphates and thiol-labelled nucleoside 5'-triphosphates.

7. The method of claim 1 wherein step (a) comprises activating said receptor in the presence of labelled RNA precursors selected from the group consisting of tritiated uridine, 4-thiouridine, 6-thioguanosine, and combinations thereof.

8. The method of claim 1 wherein the substance which enhances the level of RNA comprises an inhibitor of protein synthesis.

9. The method of claim 8 wherein said inhibitor of protein synthesis is selected from the group consisting of puromycin, cycloheximide, and mixtures thereof.

10. The method of claim 1 wherein the substance which enhances the level of RNA is selected from the group consisting of cyclic adenosine monophosphate (cAMP), an analog thereof, and molecules which increase the intracellular level of cAMP.

11. The method of claim 10 wherein step (a) comprises activating said receptor in the presence of dibutyl cAMP.

12. The method of claim 1 wherein step (b)comprises affinity separating said thiol-labelled RNA from said remaining RNA.

13. The method of claim 12, further comprising after step (a)
   (i) extracting cellular RNA from said activated cell;
   (ii) contacting said cellular RNA with phenylmercury agarose under conditions conductive for the binding of said thiol-labeled RNA to said agarose phenylmercury;
   (iii) removing any unbound RNA; and
   (iv) eluting the bound, thiol-labelled RNA from the phenylmercury agarose under reducing conditions.

14. The method of claim 1 further comprising (e); screening said superinduced library for clones comprising genes induced by said ligand by probing said cDNA library with
   a DNA probe constructed from mRNA derived from a receptor-activated cell; and
   a DNA probe constructed from mRNA derived from an unactivated cell.
   said superinduced library being probed under conditions effective for said DNA probes to hybridizes specifically with complementary cDNA sequences present in said library.

15. A method of selecting for, isolating, and identifying a ligand-inducible gene in a cell, comprising:
   (I) the method of claim 1; and
   (II) identifying the genes from which said thiol-labelled RNA was transcribed in response to ligand induction by screening said superinduced library for clones which hybridize to a DNA probe constructed from mRNA derived from a receptor-activated cell, and fail to hybridize to a DNA probe constructed from mRNA derived from an unactivated cell, under stringent conditions.

16. The method of claim 15 wherein step (II) comprises screening said library with a first DNA probe constructed from said thiol-labelled RNA under conditions effective so that said probe hybridizes with cDNA sequences in said library;

screening said library with a second DNA probe constructed from RNA from uninduced cells under conditions effective so that said probe hybridizes with cDNA sequences in said library; and selecting cDNA clones which hybridize to said first DNA probe but not to said second DNA probe.

17. The method of claim 1, wherein the cellular receptor is a mammalian receptor.

18. method according to claim 1 wherein step (c) is conducted with oligo-dT primers.

19. A method of producing a superinduced complementary DNA (cDNA) library enriched for interleukin-2-inducible genes of a cell, comprising:

(a) activating an interleukin-2 receptor on a cell by exposing said cell to IL-2 for a predetermined period in the presence of thiol-labeled RNA precursors, radiolabelled RNA precursors, and cycloheximide;

(b) separating the thiol-labeled RNA transcribed during the period of exposure to IL-2 from the remaining RNA by affinity chromatography using phenylmethyl mercury agarose;

(c) preparing cDNA from said thiol-labeled RNA, and selecting fragments greater than 500 bp; and (d) cloning said cDNA in host cells to produce a superinduced cDNA library.

20. The method of claim 19, further comprising (e) screening said superinduced library for clones of genes activated by IL-2 by probing said superinduced cDNA library with a first DNA probe constructed from messenger RNA (mRNA) derived from an IL-2-receptor-activated cell and a second DNA probe constructed from mRNA derived from an unactivated cell, said superinduced library being probed under conditions effective for said DNA probes to hybridize specifically with complementary cDNA sequences in said library; and (f) selecting cDNA clones which hybridize to said first probe but not to said second probe.

21. A method of selecting for, isolating, and identifying a ligand-inducible gene in a cell, comprising (a) activating a cellular ligand receptor for a predetermined period of time in the presence of
(i) thiol-labeled RNA precursors which are incorporated into the RNA synthesized by said cell in response to receptor activation, and
a substance which enhances the level of RNA in said cell;

(b) separating the thiol-labeled RNA from the remaining RNA;

(c) preparing cDNA from said labeled RNA, and selecting fragments treater than 500 bp; and (d) cloning said cDNA in host cells to provide a superinduced cDNA library; and (e) screening said superinduced cDNA library for clones containing genes induced by said ligand.

22. The method of claim 21, wherein said cell is mammalian.

23. The method of claim 21, wherein step (e) is conducted by screening the superinduced library with a first probe comprising DNA constructed from the thiol-labelled mRNA, and with a second probe comprising cDNA constructed from mRNA from uninduced cells; and selecting clones that hybridize to the first probe but not to the second probe under stringent hybridization conditions.

24. A superinduced cDNA library comprising fragments greater than 500 bp enriched for genes whose expression is induced in response to a ligand-cellular receptor interaction, said library being constructed from affinity-separated thiol-labelled mRNA transcribed in a cell in the presence of a substance that enhances the level of RNA in the cell, in response to the ligand-receptor interaction.

25. The cDNA library of claim 24 constructed from mRNA in the presence of a substance which enhances the level of mRNA in the cell.

26. The cDNA library of claim 24 constructed from mRNA transcribed in response to IL-2 activation of the interleukin-2 receptor (IL-2R).

27. The cDNA library of claim 26 wherein the substance that enhances the level of RNA in the cell comprises cycloheximide.

28. A cDNA library obtained by a method comprising the steps of:

(a) activating a cellular ligand receptor of a cell for a predetermined period of time in the presence of thiol-labeled RNA precursors which are incorporated into the RNA synthesized by said cell in response to receptor activation and a substance which enhances the level of RNA in said cell;

(b) separating the thiol-labeled RNA from the remaining RNA;

(c) preparing cDNA from said labeled RNA, selecting fragments greater than 500 bp; and (d) cloning said selected cDNA in host cells to obtain said cDNA library.

29. A cDNA library according to claim 28, wherein said cell is mammalian.

30. A cDNA library according to claim 28, wherein the receptor is activated by a ligand selected from the group consisting of cytokines, antibodies, peptides, and receptor-binding fragments thereof.

31. A cDNA library according to claim 30, wherein said ligand is a cytokine selected from the group consisting of the interleukins, cellular growth factors, colony stimulating factors, and hormones.

32. A cDNA library according to claim 31, wherein said cytokine is IL-2.

33. A cDNA library obtained by a method comprising the steps of:

(a) activating an interleukin-2 receptor on a cell by exposing said cell to IL-2 for a predetermined period in the presence of thiol-labeled RNA precursors, radiolabelled RNA precursors, and cycloheximide;

(b) separating the thiol-labeled RNA transcribed during the period of exposure to IL-2 from the remaining RNA by affinity chromatography using phenylmethyl mercury agarose;

(c) preparing cDNA from said thiol-labeled RNA, and selecting fragments greater than 500 bp; and (d) cloning said cDNA in host cells to produce said cDNA library.

* * * * *